United States Patent [19]

Day

[11] Patent Number: 4,652,251
[45] Date of Patent: Mar. 24, 1987

[54] DETERMINING THE DIFFERENCE BETWEEN THE TEMPERATURE OF A LIQUID FLOWING IN A CLOSED SYSTEM AND ITS SATURATION TEMPERATURE

[75] Inventor: Bobby L. Day, Walldorf, Fed. Rep. of Germany

[73] Assignee: Brown Boveri Reaktor GmbH, Fed. Rep. of Germany

[21] Appl. No.: 440,905

[22] Filed: Nov. 12, 1982

[51] Int. Cl.⁴ .................. G01K 13/00; G21C 17/02
[52] U.S. Cl. ............................. 374/101; 374/143; 376/247
[58] Field of Search ............ 374/143, 101, 110; 376/247

[56] References Cited

U.S. PATENT DOCUMENTS

| | | | |
|---|---|---|---|
| 2,813,419 | 11/1957 | Harrison | 374/110 X |
| 4,197,990 | 4/1980 | Carberg et al. | 374/101 X |
| 4,278,051 | 7/1981 | Shida | 376/247 X |
| 4,394,346 | 7/1983 | Morooka | 376/246 X |
| 4,405,559 | 9/1983 | Tokarz | 376/247 |

FOREIGN PATENT DOCUMENTS 1053371 12/1962 United Kingdom ............... 374/143

Primary Examiner—Daniel M. Yasich
Attorney, Agent, or Firm—Robert J. Edwards; Kenneth W. Iles; D. Neil LaHaye

[57] ABSTRACT

A method of determining with improved accuracy, the temperature margin to saturation of a heated pressurized liquid or vapor contained in a closed system. This method is characterized by the utilization of a direct measurement of the pressure margin to saturation instead of a measurement of the actual pressure of the system. The actual temperature of the system is used to determine the appropriate portion of the saturation curve to be used for the conversion of the pressure margin to saturation to the temperature margin to saturation.

9 Claims, 5 Drawing Figures

DETERMINING THE DIFFERENCE BETWEEN THE TEMPERATURE OF A LIQUID FLOWING IN A CLOSED SYSTEM AND ITS SATURATION TEMPERATURE

BACKGROUND OF THE INVENTION

1. Field of the Invention

This invention relates to a procedure for determining the difference between the temperature of a heated, pressurized liquid flowing in a closed system and its saturation temperature.

2. Description of the Prior Art

Saturation is reached in such liquids under specific pressure and temperature conditions. There are many examples of applications where it is highly desirable to have precise information concerning the saturation temperature and the difference from the saturation temperature for a pressurized, heated flowing liquid. Such an application, particularly when problems occur, is the primary cooling system of a pressurized water nuclear reactor installation which has a pressure of about 2350 psi and a temperature of about 570° F. When temperature instruments with a range of about 300° F.–680° F. and pressure instruments with a range of about 150 psi–2600 psi must be used, as in this example, it is difficult to determine pressure and temperature data precisely because of these wide ranges. That is, a typical pressure transmitter alone exhibits a measurement uncertainty on the order of plus or minus 1 lb./100 lbs. of range, so that a pressure transmitter having a range of 0– 2,500 lbs./in.$^2$ has an expected uncertainty error on the order of at least 25 lbs./in.$^2$ over its entire normal operating range. Similar measurement uncertainty is introduced by temperature measurements.

The difference between saturation temperature and actual temperature of the liquid becomes especially important, however, when that difference is relatively small, i.e., when accident conditions prevail. If saturation temperature is reached the liquid will boil, thereby reducing its ability to conduct heat from heating elements, such as fuel rods. Further, under accident conditions, the accuracy of measurements of temperature and pressure deteriorates substantially. If, for example, pressure measurement string uncertainty of 2%–3% can be achieved over a broad range under normal operating conditions, an uncertainty of 12%–15% will probably be reached under accident conditions, i.e., by increased temperature, humidity, and radiation level of the transmitter environment.

It is generally known how to establish the difference between the temperature and the saturation temperature of a liquid in the following manner. The pressure of the liquid is measured, and is converted into the pertinent saturation temperature electronically or digitally, on the basis of a precalculated or otherwise known saturation curve. The temperature of the liquid is then measured and the differential between the calculated saturation temperature and the measured actual temperature of the liquid is taken.

Because of the large ranges of the measuring devices and the combination of the pressure and temperature measurement methods with one another, the measurement errors are additive, so that no reliable statement concerning the temperature difference from the saturation temperature is possible. Under accident conditions, the much greater measurement errors further reduce meaningfulness and usefulness of the computed temperature difference from saturation.

It is therefore apparent that a substantial need exists for a method of more accurately determining the difference between the temperature of a heated pressurized liquid flowing in a closed system and its saturation temperature.

SUMMARY OF THE INVENTION

This invention describes a procedure which provides more precise measurement of the difference between the temperature and saturation temperature of a liquid. This problem is solved pursuant to the invention by converting the pressure margin between the liquid pressure and the associated saturation pressure, which is independently measured by a known type of relative pressure device such as that described in U.S. patent application Ser. No. 06/354,412 filed Mar. 3, 1982 to the temperature margin between the fluid temperature and saturation temperature using the saturation curve. A measured temperature is used to index the conversion to the appropriate part of the saturation curve (a pressure could also be used but would provide a less accurate result).

With the proposed combination of measurement steps, no direct addition of the individual measurement errors takes place. Any inaccuracy in the temperature measurement has little effect on the calculated margin to saturation temperature because the relevant portion of the saturation curve has very little change of slope within the measurement uncertainty of the index parameter. The inaccuracy from the pressure margin differential pressure measurement is substantially smaller than a pressure measurement would be, since it has a much smaller range than a pressure measurement of the liquid.

These and other aspects of the present invention will be more clearly understood upon review of the following description of the preferred embodiment considered with the drawings.

Figure 1:
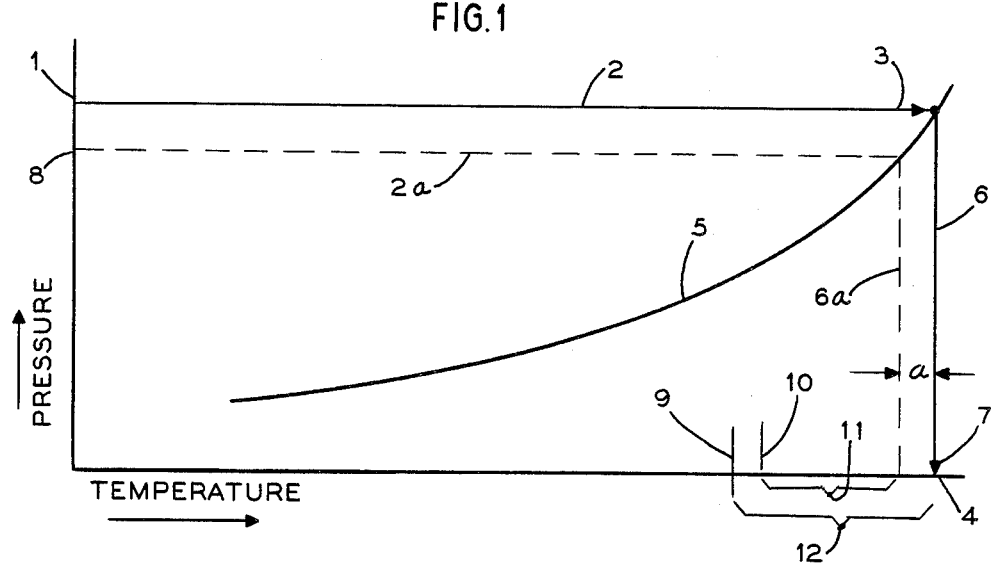
FIG. 1 illustrates the procedure according to the present state of the art.

The procedure according to the state of the art of the additivity of errors occuring therein are illustrated in FIG. 1. A pressure measurement of the fluid or liquid to be monitored produces the pressure value 1. The associated saturation temperature 4 is determined from this pressure value, as shown by the line 2 and the arrow 3. The known saturation curve 5 for the liquid is used for this purpose, by drawing the line 6 in the direction of the arrow 7 from its intersection with the line 2. If any inaccuracy occurs in the pressure measurement, which leads, e.g., to a pressure value 8, this produces an inaccuracy in calculated saturation temperature 4, as illustrated by the lines 2a, 6a and represented by the error dimension "a". Direct measurement of the temperature of the liquid may produce the correct temperature value, e.g., 9 in or an incorrect temperature value, e.g., 10 in another case. The inaccuracies from the pressure and temperature measurements are additive and lead to a figure for the margin from the saturation temperature which can have either the value 11 or the value 12. In practice, with the wide ranges of the temperature and pressure indicators mentioned initially, in unfavorable cases this means inaccuracies on the order of plus or minus 30°–35° F. in the saturation temperature margin measurement.

Figure 2:
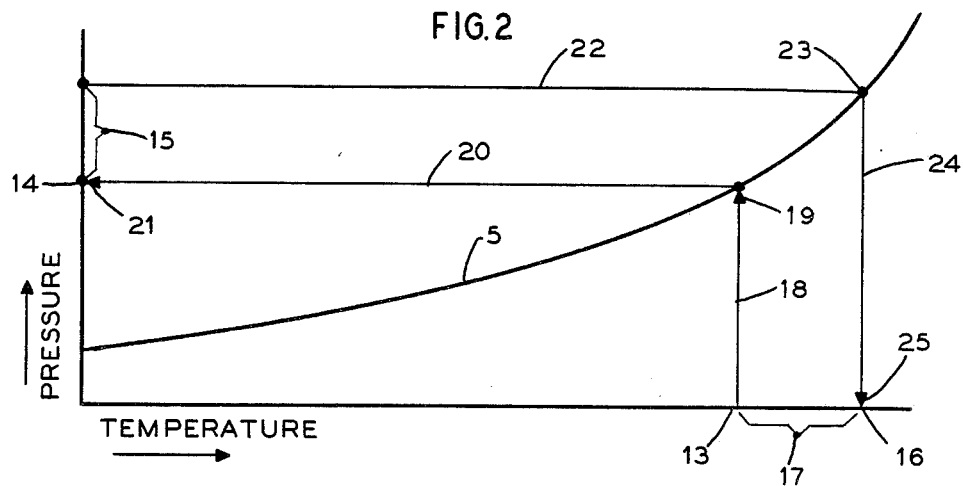
FIG. 2 illustrates the procedure according to the present invention.
Figure 5:
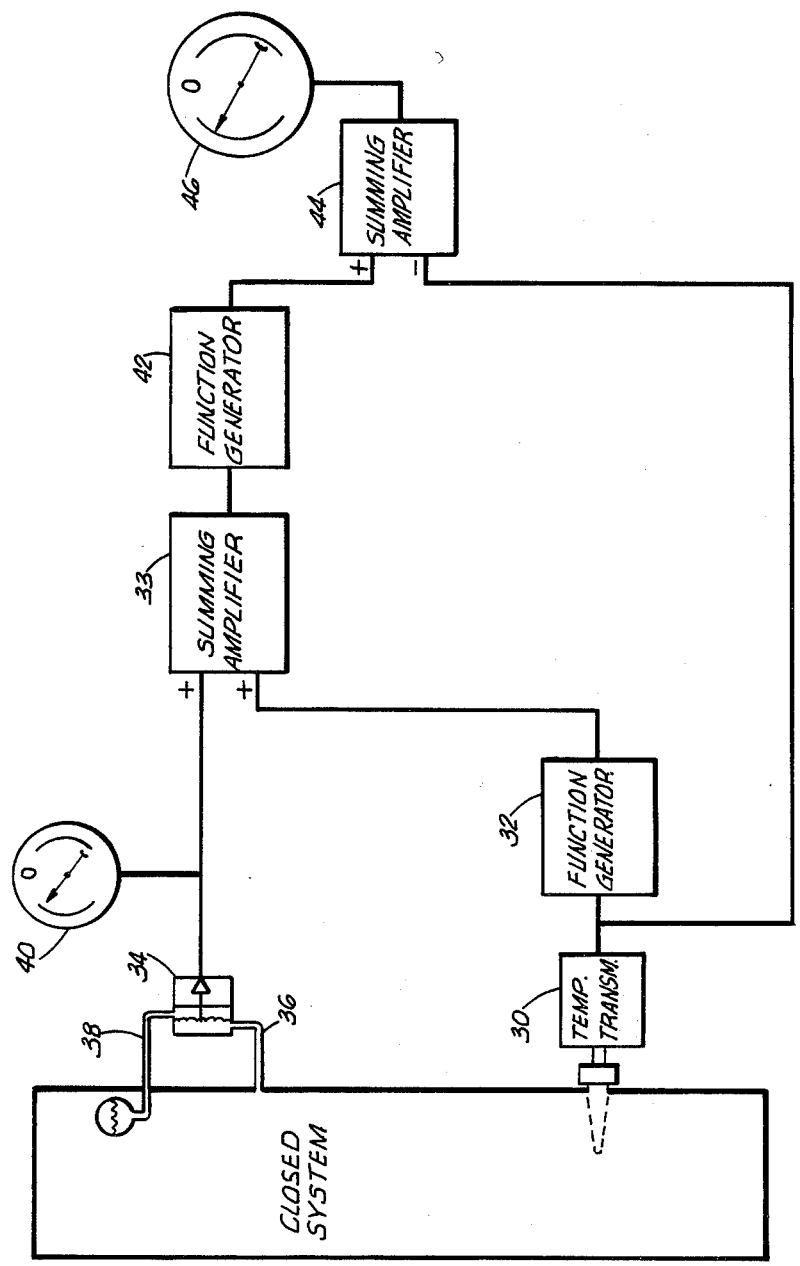
FIG. 5 illustrates a schematic drawing of the invention.

FIGS. 2 and 5 shows the new procedure for the more precise determination of the temperature margin from saturation temperature. The procedure here is carried out in the following steps.

A. The temperature of the liquid is measured, by the use of temperature detector means 30 such as a resistance temperature detector, a thermo-couple, a capillary tube vapor pressure thermometer, or any other temperature detector capable of developing a control signal proportional to temperature and the associated saturation pressure 14 is electronically derived from this temperature value 13 by using a function generator 32 consisting of multiple linear segments derived from multiple measurements or from one of the curves approximating the desired function which in this case is the saturation curve 5. This step is symbolized by the line 18 with the arrow 19 and by the line 20 with the arrow 21 in FIG. 2 and FIG. 5.

B. To this value of the associated saturation pressure is added the value of pressure margin 15 between the liquid pressure and the associated saturation pressure by first summing amplifier 33. Pressure margin 15, or differential pressure to saturation, can be electronically determined through means known to the art such as a relative pressure device. A differential pressure measuring transducer 34 is connected directly to the primary coolant via conduit 36 and indirectly to the coolant via coolant filled and sealed sensing conduit 38. Transducer 34 senses the pressure difference between conduit 36 at actual system pressure and conduit 38 at saturation pressure to provide the pressure margin 15 to saturation at gauge 40.

C. Using the saturation curve 5, saturation temperature 16 corresponding to the sum of these pressure values 14 and 15 is found by function generator 42. Lines 22 and 24 with arrows 23 and 25 illustrate this step.

D. The difference between this saturation temperature 16 and measured temperature 13 of the liquid determined by second summing amplifier 44 and indicated by gauge 46, represents in a known way temperature margin 17 from the saturation temperature 16.

Figure 3:
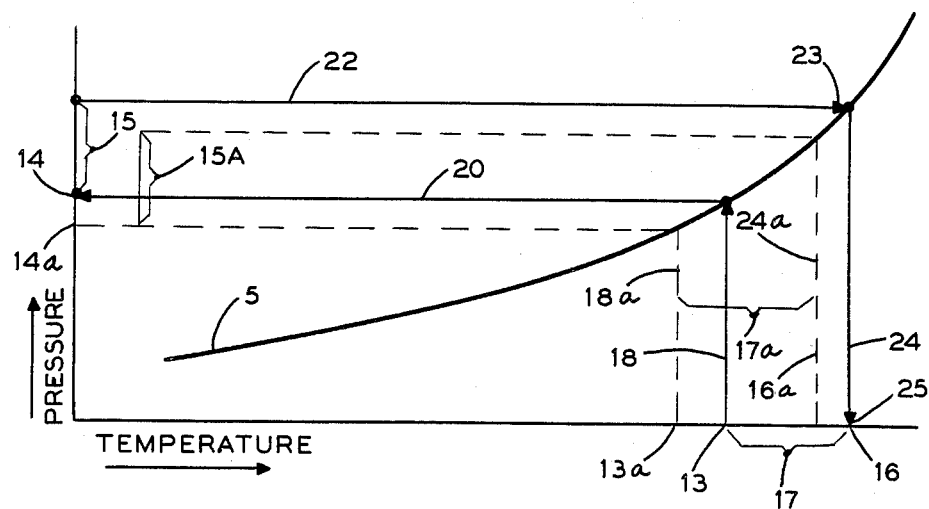
FIG. 3 illustrates how the effect of measurement errors of the indexing parameter (temp.) are minimized according to the present invention.

Using FIG. 3, it will be explained why the effect of inaccuracies in the temperature measurement is largely excluded in the proposed procedural steps. If actual temperature value 13 because of an inaccurate measurement device, results in the measured temperature value 13a, the associated saturation pressure 14a derived from this will indeed also turn out to be lower. However, since the pressure margin 15 is a constant figure, i.e., does not depend on measured temperature 13a in any fashion, the derivation of saturation temperature 16a from the sum of the saturation pressure 14a and the pressure margin 15 produces a compensating error resulting in only a negligibly small change in temperature margin 17, which results from the nonlinear shape of the saturation curve. The temperature margin 17a defined by the lines 18a and 24a is therefore substantially equal to the temperature margin 17 defined by the lines 18 and 24.

Figure 4:
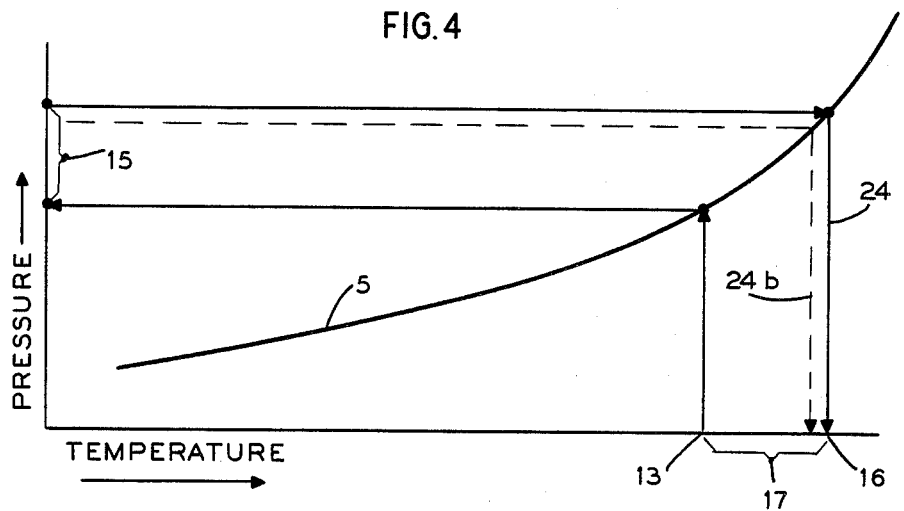
FIG. 4 illustrates the effect of the differential pressure measurement error of the inventive method.

The effect from the pressure margin value 15 shown in FIG. 4 remains as the only noteworthy inaccuracy. The pressure margin value extends over a substantially smaller range than the liquid pressure. Consequently, the range of the measurement devices necessary for this is adapted to the particular range. The inaccuracy is therefore substantially smaller for the pressure margin value 15 than that for the liquid pressure as illustrated in FIG. 1.

The distance between the lines 24 and 24b illustrated in FIG. 4 symbolizes this inaccuracy, which is smaller than the distance "à" of FIG. 1 also resulting from the pressure measurement. In practice, the inaccuracy from FIG. 4 is only approximately 5% of the inaccuracy of FIG. 1.

It has therefore been possible with the procedure pursuant to the invention to describe the temperature margin from the saturation temperature substantially more precisely. The inaccuracy from the temperature measurement has been excluded and the inaccuracy from the pressure measurement has been reduced by a factor of 20. The temperature margin value 17, of FIG. 4 can thus be used as a reliable paramenter for the monitoring of a system in which liquids circulate at high temperature and high pressure.

Modifications and improvements in the present invention may occur to those skilled in the art. It will be understood that the scope of the invention is limited only by the following claims.

What is claimed is:

1. A method for determining the difference between the temperature of a heated, pressurized liquid flowing in a closed system and its saturation temperature, comprising:
   a. measuring the temperature of said liquid;
   b. electronically deriving the saturation pressure of said liquid associated with said measured temperature through the use of a first function generator consisting of multiple linear segments approximating the saturation curve of said liquid;
   c. determining the pressure margin to saturation pressure by pressure measurements utilizing a relative pressure device comprising a differential pressure measuring transducer connected directly to the pressurized liquid and indirectly to the pressurized liquid via a sealed liquid filled conduit at saturation pressure;
   d. electronically adding said derived saturation pressure with said determined pressure margin in a first summing amplifier to derive the actual pressure of said fluid;
   e. electronically deriving the saturation temperature of said liquid associated with said derived actual pressure through the use of a second function generator consisting of multiple linear segments approximating the saturation curve of said liquid; and
   f. electronically subtracting said measured temperature from said derived saturation temperature in a second summing amplifier to obtain the difference between the actual temperature and saturation temperature of said liquid.

2. A method for determining the difference between the temperature of a heated, pressurized liquid flowing in a closed system and its saturation temperature, comprising:
   a. measuring the temperature of said fluid;

b. electronically deriving the saturation pressure of said liquid associated with said measured temperature;
c. determining the pressure margin to saturation pressure by direct pressure measurements of said liquid utilizing a relative pressure device;
d. electronically adding said derived saturation pressure with said determined pressure margin to derive the actual pressure of said fluid;
e. electronically deriving the saturation temperature of said liquid associated with said derived actual pressure; and
f. electronically substracting said measured temperature from said derived saturation temperature to obtain the difference between the actual temperature of said liquid and its saturation temperature.

3. The method of claim 2 wherein the step of deriving the saturation pressure is accomplished electronically by comparison of said measured temperature with a saturation curve.

4. The method of claim 2 wherein said relative pressure device comprises a differential pressure measuring transducer connected directly to the pressurized liquid and indirectly to the pressurized liquid.

5. The method of claim 2 wherein the step of deriving the actual pressure utilizes a first summing amplifier.

6. The method of claim 2 wherein the step of deriving the associated saturation temperature utilizes electronic comparison of said derived actual pressure with a saturation curve.

7. The method of claim 2 wherein the step of subtracting said measured temperature from said derived saturation temperature utilizes a second summing amplifier.

8. A method for determining the difference between the temperature of a heated, pressurized liquid flowing in a closed system and its saturation temperature, comprising:
a. measuring the temperature of said liquid;
b. electronically deriving the saturation pressure of said liquid associated with said measured temperature through the use of a first function generator;
c. determining the pressure margin to saturation pressure by pressure measurements utilizing a relative pressure device comprising a differential pressure measuring transducer connected directly to the pressurized liquid and indirectly to the pressurized liquid;
d. electronically adding said derived saturation pressure with said determined pressure margin in a first summing amplifier to derive the actual pressure of said fluid;
e. electronically deriving the saturation temperature of said liquid associated with said derived actual pressure through the use of a second function generator; and
f. electronically subtracting said measured temperature from said derived saturation temperature in a second summing amplifier to obtain the difference between the actual temperature and saturation temperature of said liquid.

9. The method of claim 8 wherein said first and second function generators consist of multiple linear segments approximating the saturation curve of said liquid.

* * * * *